(12) United States Patent
Fischell et al.

(10) Patent No.: US 6,716,240 B2
(45) Date of Patent: Apr. 6, 2004

(54) STENT HAVING A MULTIPLICITY OF UNDULATING LONGITUDINALS

(75) Inventors: Robert E. Fischell, Dayton, MD (US); David R. Fischell, Fair Haven, NJ (US); Tim A. Fischell, Nashville, TN (US)

(73) Assignee: Cordis Corporation, Miami Lakes, FL (US)

( * ) Notice: Subject to any disclaimer, the term of this patent is extended or adjusted under 35 U.S.C. 154(b) by 95 days.

(21) Appl. No.: 10/345,531

(22) Filed: Jan. 16, 2003

(65) Prior Publication Data

US 2003/0114868 A1 Jun. 19, 2003

Related U.S. Application Data

(63) Continuation of application No. 09/596,074, filed on Jun. 16, 2000, which is a continuation of application No. 09/263,518, filed on Mar. 5, 1999, now Pat. No. 6,086,604, which is a continuation of application No. 08/864,221, filed on May 28, 1997, now Pat. No. 5,879,370, which is a continuation of application No. 08/202,128, filed on Feb. 25, 1994, now Pat. No. 5,643,312.

(51) Int. Cl.[7] ............................................. A61M 29/00
(52) U.S. Cl. ...................................... 623/1.16; 606/198
(58) Field of Search ................................. 623/1.16, 1.1, 623/1.15, 1.17, 1.2, 12; 606/198, 1, 194, 195

(56) References Cited

U.S. PATENT DOCUMENTS

| 3,657,744 A | 4/1972 | Ersek |
| 4,503,569 A | 3/1985 | Dotter |
| 4,553,545 A | 11/1985 | Maass et al. |
| 4,580,568 A | 4/1986 | Gianturco |

(List continued on next page.)

FOREIGN PATENT DOCUMENTS

| EP | 593136 | 12/1989 |
| EP | 433011 | 6/1991 |
| EP | 472731 | 3/1992 |
| EP | 0540290 A2 * | 10/1992 |
| EP | 540290 | 5/1993 |
| EP | 566807 | 10/1993 |
| EP | 579523 | 1/1994 |
| GB | 1205743 | 9/1970 |
| GB | 2189150 | 10/1987 |
| JP | 6-41745 | 6/1994 |
| WO | WO95/31945 | 11/1995 |

OTHER PUBLICATIONS

Lawrence et al., "Percutaneous Endovascular Graft:Experimental Evaluation," 1987 RSNA Annual Meeting, *Radiology,* vol. 163, pp. 357–360 (May 1987).

Mirich et al., "Percutaneously Placed Endovascular Grafts for Aortic Aneurysms:Feasibility Study," *Radiology,* vol. 170, pp. 1033–1037.

Fallone et al., "Elastic Characteristics of the Self–Expanding Metallic Stents," *Investigative Radiology,* vol. 23, pp. 370–376. (May 1988).

(List continued on next page.)

*Primary Examiner*—Marvin M. Lateef
*Assistant Examiner*—Ruby Jain
(74) *Attorney, Agent, or Firm*—Wood, Phillips, Katz, Clark & Mortimer

(57) ABSTRACT

A stent which is adapted for placement in the vessels of a human body is provided. The stent may be in the form of a thin-walled metal cylinder having a longitudinal axis. The stent has a proximal end and a distal end and includes a number of circumferentially relatively rigid portions. The relatively rigid portions are joined to each other by one or more longitudinals which extend in a substantially longitudinal direction. At least a portion of at least one of the longitudinals has an undulating shape where a first relatively rigid portion is located at the proximal end of the stent and a second relatively rigid portion is located at the distal end of the stent.

66 Claims, 4 Drawing Sheets

U.S. PATENT DOCUMENTS

| | | |
|---|---|---|
| 4,655,771 A | 4/1987 | Wallsten |
| 4,681,110 A | 7/1987 | Wiktor |
| 4,733,665 A | 3/1988 | Palmaz |
| 4,739,762 A | 4/1988 | Palmaz |
| 4,768,507 A | 9/1988 | Fischell |
| 4,795,458 A | 1/1989 | Regan |
| 4,800,882 A | 1/1989 | Gianturco |
| 4,830,003 A | 5/1989 | Wolff |
| 4,856,516 A | 8/1989 | Hillstead |
| 4,878,906 A | 11/1989 | Lindemann et al. |
| 4,886,062 A | 12/1989 | Wiktor |
| 4,907,336 A | 3/1990 | Gianturco |
| 4,954,126 A | 9/1990 | Wallsten |
| 4,969,458 A | 11/1990 | Wiktor |
| 4,994,071 A | 2/1991 | MacGregor |
| 5,019,085 A | 5/1991 | Hillstead |
| 5,061,275 A | 10/1991 | Wallsten |
| 5,102,417 A | 4/1992 | Palmaz |
| 5,104,404 A | 4/1992 | Wolff |
| 5,109,090 A | 4/1992 | Mongoin et al. |
| 5,116,365 A | 5/1992 | Hillstead |
| 5,133,732 A | 7/1992 | Wiktor |
| 5,135,536 A | 8/1992 | Hillstead |
| 5,192,307 A | 3/1993 | Wall |
| 5,195,984 A | 3/1993 | Schatz |
| 5,201,901 A | 4/1993 | Harada |
| 5,266,073 A | 11/1993 | Wall |
| 5,269,802 A | 12/1993 | Garber |
| 5,282,824 A | 2/1994 | Gianturco |
| 5,290,305 A | 3/1994 | Inoue |
| 5,292,331 A | 3/1994 | Boneau |
| 5,314,472 A | 5/1994 | Fontaine |
| 5,405,377 A | 4/1995 | Cragg |
| 5,421,955 A | 6/1995 | Lau et al. |
| 5,443,498 A | 8/1995 | Fontaine |
| 5,443,500 A | 8/1995 | Sigwart |
| 5,449,373 A | 9/1995 | Pinchasik |
| 5,496,365 A | 3/1996 | Sgro |
| 5,507,767 A | 4/1996 | Maeda et al. |
| 5,507,771 A | 4/1996 | Gianturco |
| 5,514,154 A | 5/1996 | Lau et al. |
| 5,527,354 A | 6/1996 | Fontaine et al. |
| 5,569,295 A * | 10/1996 | Lam .......................... 606/198 |
| 5,591,197 A * | 1/1997 | Orth et al. .................. 623/1.16 |
| 5,603,721 A | 2/1997 | Lau et al. |
| 5,632,771 A | 5/1997 | Boatman et al. |
| 5,674,278 A | 10/1997 | Boneau |
| 5,733,303 A * | 3/1998 | Israel et al. ................. 623/1.15 |
| 5,879,370 A * | 3/1999 | Fischell et al. ............. 623/1.16 |
| 6,547,817 B1 * | 4/2003 | Fischell et al. ............. 623/1.16 |

OTHER PUBLICATIONS

Charnsangavej et al., "Stenosis of the Vena Cava:Preliminary Assessment of Treatment with Expandable Metallic Stents," *Radiology,* 1986 161:295–98.

Rosch et al., "Gianturco Expandable Stents in Experimental and Clinical Use," Mar. 24, 1987, pp. 121–124.

Wallace et al., "Tracheobronchial Tree:Expandable Metallic Stents Used in Experimental and Clinical Applications Work in Progress," *Radiology,* 158:309–12 (1986).

Rosch et al., "Experimental Intraheptic Protacaval Anastomosis: Use of Expandable Gianturco Stents," *Radiology,* 162:481–85 (1987).

Rosch et al., "Modified Gianturco Expandable Wire Stents in Experimental and Clinical Use," *Ann Radiol,* 31:100–03 (1988).

Charsangavej, et al., "A New Expandable Metallic Stent for Dilation of Stenotic Tubular Structures Experimental and Clinical Evaluations," *Houston Medical Journal,* vol. 3, Jun. 1987, pp. 41–51.

Rosch et al., "Gianturco Expandable Wire Stents in the Treatment of Superior Vena Cava Syndrome Recurring After Maximum–Tolerance Radiation," *Cancer,* 60:1243–46 (1987).

Yoshioka et al., "Self–Expanding Endovascular Graft:An Experimental Study in Dogs," *AJR,* 151:673–76 (1988).

Simonds et al., "Use of Experimental Metal Stents in the Treatment of Bronchial Obstruction," *Thorax,* 44:680–81 (1989).

Duprat et al., "Flexible Balloon–Expandable Stent for Small Vessels," *Radiology,* 162:276–78 (1987).

* cited by examiner

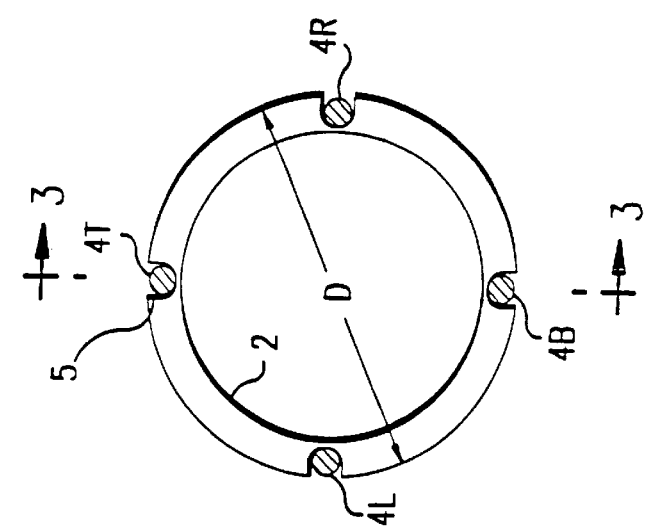
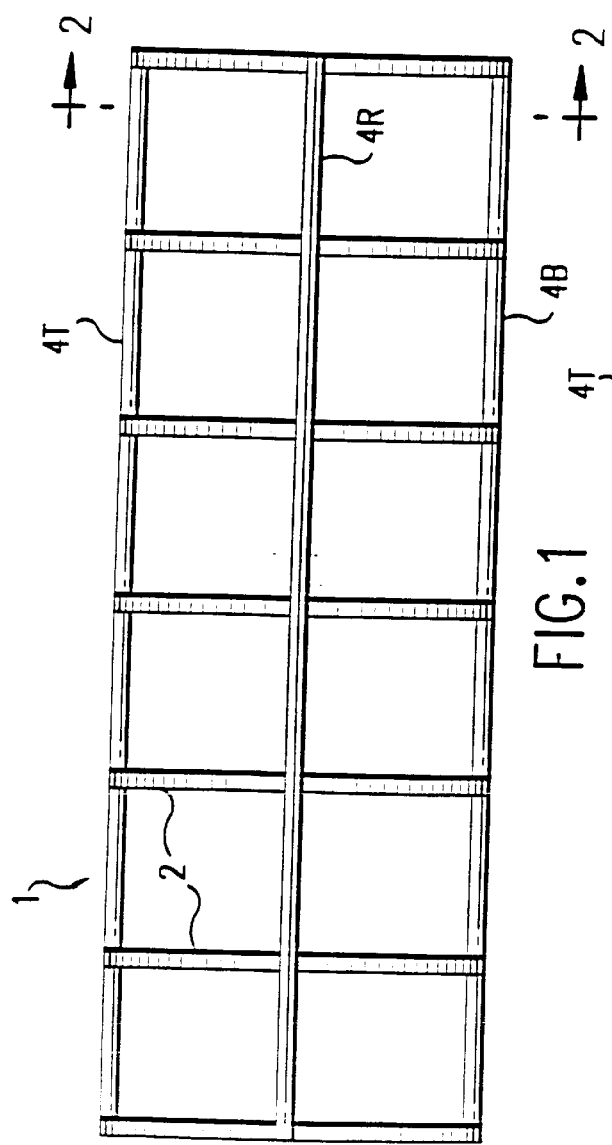
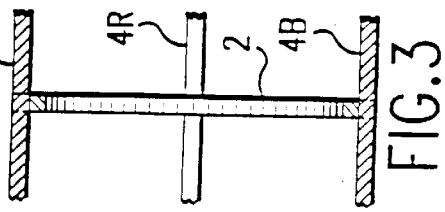
FIG.1
FIG.2
FIG.3

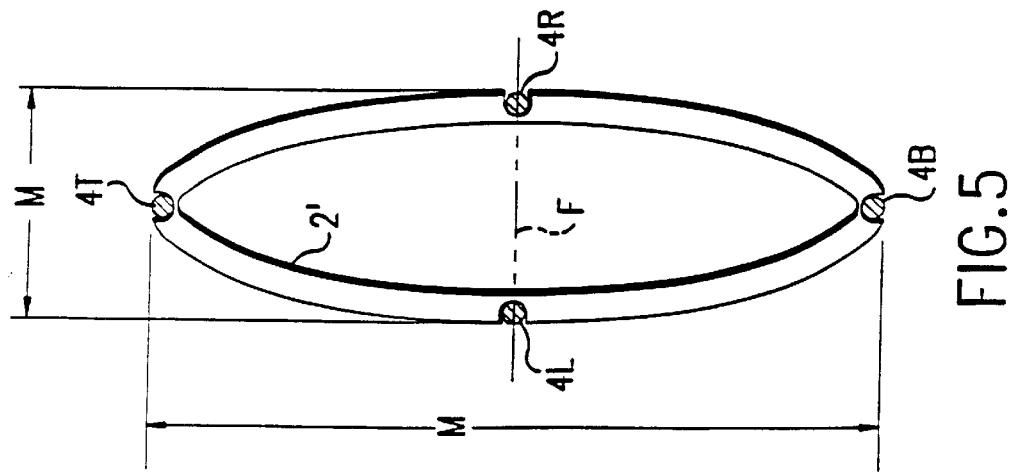
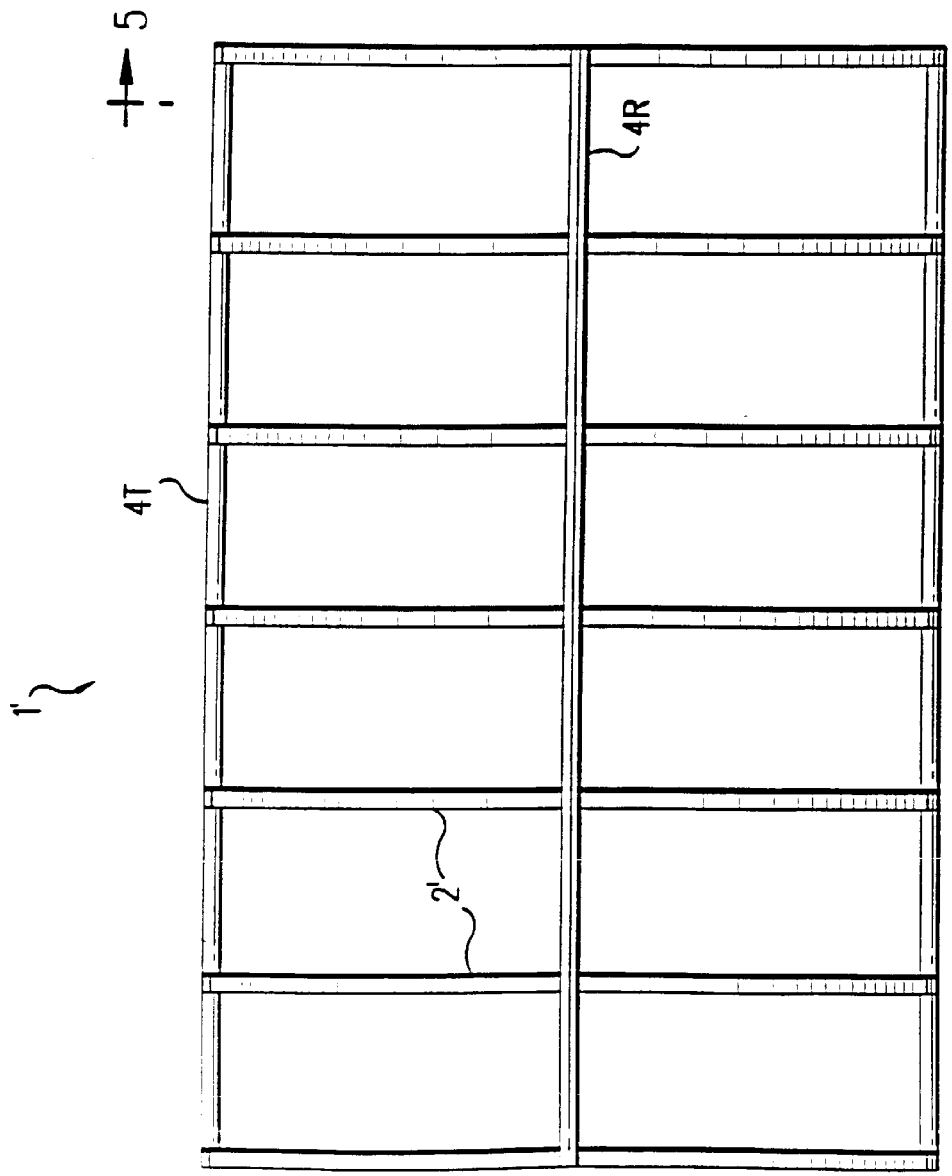

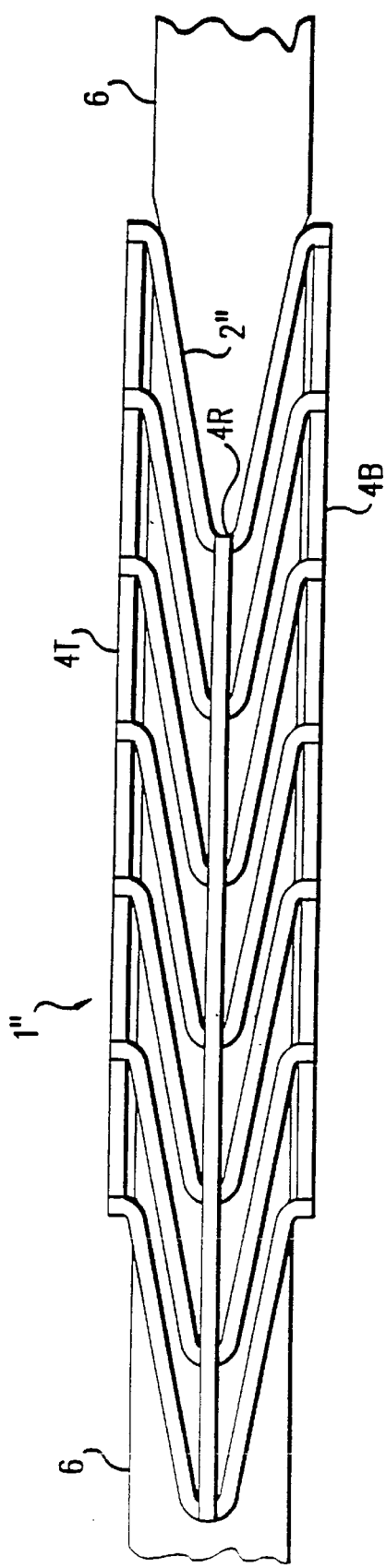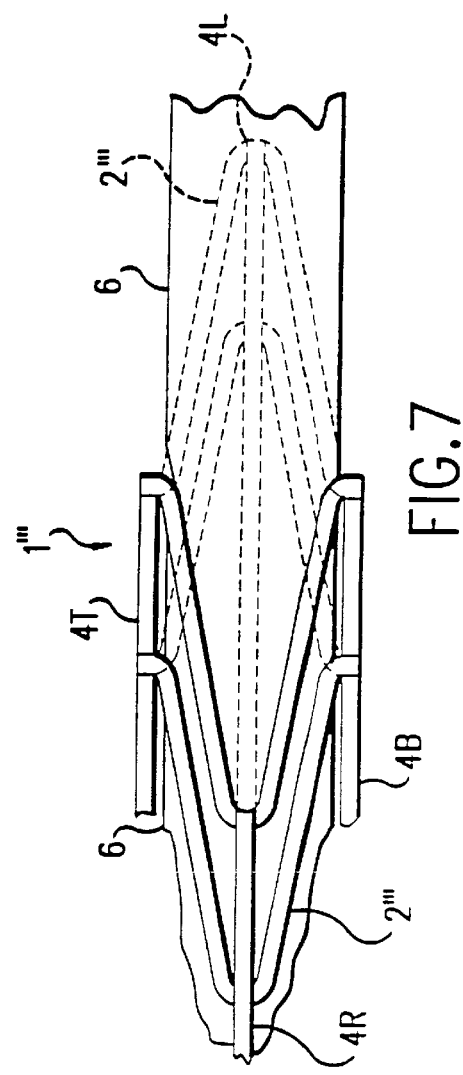

STENT HAVING A MULTIPLICITY OF UNDULATING LONGITUDINALS

This Patent Application is a Continuation of patent application Ser. No. 09/596,074 filed on Jun. 16, 2000, currently pending, which is a continuation of Ser. No. 09/263,518 filed on Mar. 5, 1999, now U.S. Pat. No. 6,086,604, which is a Continuation of patent application Ser. No. 08/864,221 filed on May 28 1997, now U.S. Pat. No. 5,879,370, which is a Continuation of patent application Ser. No. 08/202,128, filed on Feb. 25, 1994 now U.S. Pat. No. 5,643,312.

FIELD OF THE INVENTION

This invention is in the field of stents for maintaining patency of any one of a multiplicity of vessels of the human body.

BACKGROUND OF THE INVENTION

In the last decade, many different designs of stents have been used to maintain patency of arteries and other vessels of the human body. In all such devices, hoop strength is an important characteristic. Specifically, the stent must have enough hoop strength to resist the elastic recoil exerted by the vessel into which the stent is placed. The Mass stent described in the U.S. Pat. No. 4,553,545 and the Dotter stent described in U.S. Pat. No. 4,503,569 are each open helical coils. The Palmaz stent described in the U.S. Pat. No. 4,733,665 is of the "chinese finger" design. The Gianturco-Rubin stent currently sold by Cook, Inc, is another stent design which like the stents of Mass, Dotter and Palmaz does not have any closed circular member to optimize hoop strength.

The ideal arterial stent utilizes a minimum wire size of the stent elements to minimize thrombosis at the stent site after implantation. The ideal arterial stent also possess sufficient hoop strength to resist elastic recoil of the artery. Although the optimum design for maximizing hoop strength is a closed circular structure, no prior art stent has been described which has a small diameter when percutaneously inserted into a vessel and which expands into the form of multiplicity of closed circular structures (i.e. rings) when expanded outward against the vessel wall.

BRIEF SUMMARY OF THE PRESENT INVENTION

The present invention is an expandable stent that can be used in an artery or any other vessel of the human body which, when expanded, forms a multiplicity of generally circular rings whose closed structure optimizes hoop strength so as to minimize elastic recoil of the vessel into which the stent is inserted. Furthermore, the structure of the stent in the present invention is initially in the form of folded ellipses or ovals which can be formed to a small diameter for percutaneous insertion by means of a stent delivery catheter. The ovals are joined to each other by either a straight or undulating shaped wires which are called "longitudinals" which serve to space the deployed rings within the vessel. Straight longitudinals are used in straight vessels and undulating longitudinals can be employed in either straight or highly curved vessels such as some coronary arteries.

Thus, an object of this invention is to provide a stent having a maximum hoop strength by the employment of closed, generally circular structures which are in fact rings.

Another object of this invention is that the rings are initially in the form of ovals that can be folded to fit onto a cylindrical structure at a distal portion of a stent delivery catheter.

Still another object of this invention is that the fully deployed rings are spaced apart by means of longitudinals which are either straight of undulating wires that are placed to be generally parallel to the longitudinal axis of the vessel into which the stent is deployed.

Still another object of this invention is that the pre-deployment stent structure is formed as a single piece out of a metal tube having a smaller inside diameter as compared to the outside diameter of an expandable balloon onto which the pre-deployment stent is mounted.

These and other important objects and advantages of this invention will become apparent from the detailed description of the invention and the associated drawings provided herein.

BRIEF DESCRIPTION OF THE DRAWINGS

FIG. 1 is a side view of the stent after it has been deployed; i.e., in its post-deployment form.

FIG. 2 is a transverse cross section of section 2—2 of FIG. illustrating how the longitudinals are joined to the rings.

FIG. 3 is a cross section at section 3—3 of FIG. 2 showing the joining of a single ring to the longitudinals.

FIG. 4 is a side view of the stent prior to being mounted onto a stent delivery catheter, i.e., in the form of an initial structure.

FIG. 5 is a transverse cross section of section 5—5 of FIG. 4 illustrating how the longitudinals are joined to the ovals.

FIG. 6 is a side view of a pre-deployment form of the stent structure in which the ovals have been folded into a small diameter cylinder that is placed around a deflated balloon situated near the distal end of a stent delivery catheter.

FIG. 7 is a partial side view of a pre-deployment stent structure showing only two of a multiplicity of folded ovals formed around an expandable balloon in which the ovals are folded in an alternative manner as compared with FIG. 6.

DETAILED DESCRIPTION OF THE DRAWINGS

Figure 8:
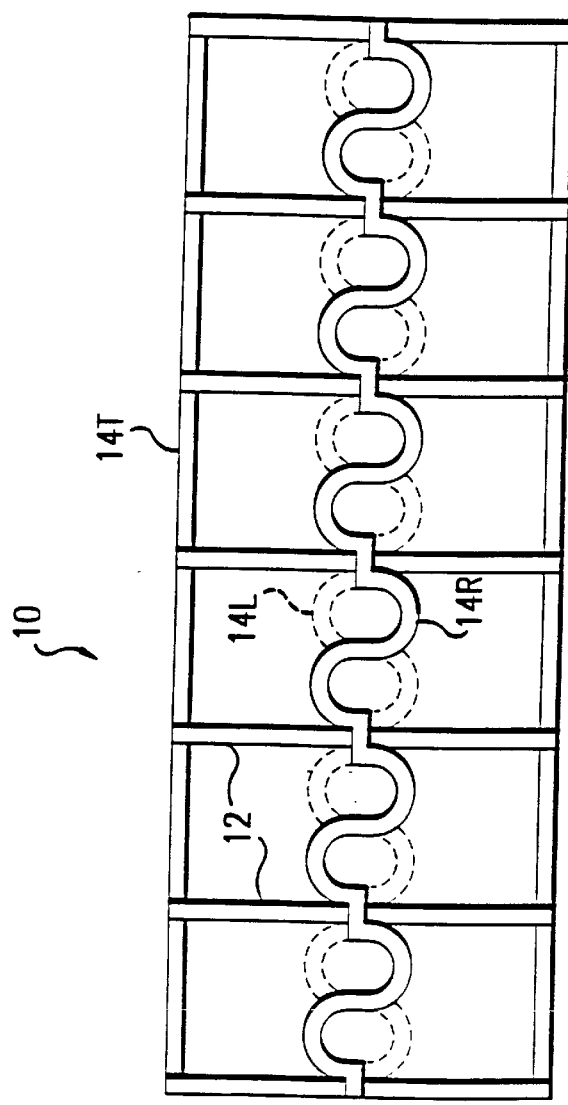
FIG. 8 is a side view of a post-deployment stent structure which utilizes two undulating longitudinals on opposite sides of the stent for improved placement in curved vessels.

FIG. 1 is a side view of the cylindrical stent 1 of the present invention shown in its post-deployment configuration. The stent 1 has a multiplicity of rings 2 which are spaced apart by four wires called longitudinals. As seen in FIGS. 1 and 2, at the top of the stent is longitudinal 4T, at the bottom is longitudinal 4B, at the left side is longitudinal 4L and at the right side is longitudinal 4R. Although FIGS. 1 and 2 show 7 rings and 4 longitudinals, it is apparent that the stent can be made longer by adding rings or increasing the separation between rings. In a similar manner, the stent can be made shorter by reducing the number of rings or decreasing the spacing between rings. Also variable spacing of the rings is envisioned for accomplishing a variety of purposes including increased hoop strength at a particular section of the stent. Also, it is envisioned that the two or more longitudinals could be utilized for this stent design with a maximum number being 32.

FIGS. 2 and 3 illustrate the joining of the longitudinals to the rings. Specifically the longitudinals can be placed into cutouts in the form of notches 5 located on the outside perimeter of the ring 2. The longitudinals can then be spot welded, adhesively bonded or joined by any variety of means to the rings 2. It is also envisioned that the longitudinals could be placed on the inside perimeter of the ring 2, or holes could be mechanically or laser drilled through the ring 2 for placement therethrough of the longitudinals.

FIGS. 4 and 5 illustrate a stent 1' shown in one particular form in which it could be fabricated; i.e., in an initial structure form. Specifically, FIGS. 4 and 5 show that this initial form of the stent 1' is a multiplicity of parallel ellipses or ovals 2" each oval having the same minor axis dimension m and major axis dimension M. The oval's minor axis passes through the center of the longitudinals 4L and 4R. The oval's major axis passes through the center of the longitudinals 4T and 4B. It is important to note that, if it is desired to have a final outside diameter D (as seen in FIG. 2) of the ring 2 after it is fully deployed, then it can be shown that D is given by the equation $D^2=1/2(m^2+M^2)$.

To place the stent design of FIGS. 4 and 5 onto a balloon that is mounted near the distal end of a stent delivery catheter, it is necessary to fold the ovals 2' around that balloon. Specifically, the pre-deployment cylindrical stent 1" can be formed onto an expandable balloon 6 as shown in FIG. 6 by folding the ovals 2' about the dotted line F (which is the minor axis of the oval 2') as shown in FIG. 5 Specifically, as seen in FIG. 4, the top and bottom of the ovals 2' could be held stationery while the side longitudinals 4R and 4L are pushed to the left which results in the pre-deployment structure which is shown as the stent 1" in FIG. 6. An optimum design has the folded ovals 2" as shown in FIG. 6 with the stent 1" being a cylinder whose outside diameter is equal in size to the minor axis dimension m. When the balloon 6 of FIG. 6 is expanded, the pre-deployment stent 1" structure forms the post-deployment stent 1 structure having circular rings 2 as shown in FIGS. 1 and 2.

The stent 1''' is an alternative embodiment for a pre-deployment structure of the stent of the present invention as it is placed onto a balloon. Specifically, FIG. 7 shows 2 folded rings 2''' of a multiple ring stent 1'''. The stent 1''' being formed by holding the top and bottom of the stent 1' of FIG. 4 stationery while pushing the longitudinal 4R to the left and pushing the longitudinal 4L to the right. Like the stent 1" of FIG. 6, when mounted onto a balloon, the stent 1''' has cylindrical shape with a diameter equal to the dimension m.

FIGS. 1 to 7 inclusive illustrate stents that employ longitudinals that are formed from generally straight wires. FIG. 8 shows an alternative embodiment of a stent 10 that has two undulating longitudinals. Specifically, the left side longitudinal 14L (shown as dotted lines) and the right side longitudinal 14R are each undulating shaped longitudinals. A stent such as stent 10 could have two or more undulating longitudinals. Such a stent would bend more easily during insertion into a vessel and would be more readily adaptable for placement in curved vessels such as some coronary arteries.

Typically, the rings and longitudinals of the stents would be made of the same material. Typical metals used for such a stent would be stainless steel, tantulum, titanium, or a shape memory metal such as Nitinol. If Nitinol is used, the stent would be heat treated into the shape at body temperature having circular rings 2 as shown in FIGS. 1 and 2. The rings could then be distorted into ovals as shown in FIGS. 4 and 5 and then mounted onto a stent delivery catheter which does not employ a balloon but is of the more general shape described in the previously cited U.S. Pat. No. 4,553, 545 by C. T. Dotter. Such a design would provide the desired stent structure having a multiplicity of generally circular rings instead of the Dotter design of a helical spring which inherently has a lesser hoop strength as compared to the present invention.

It should be understood that once the ovals are folded onto a stent delivery catheter, when they fully deploy, they do not form perfectly circular rings as shown in FIG. 2, but rather they are of a generally circular shape. Such comparatively small deviations form an exactly circular shape do not appreciably decrease hoop strength because they are in fact closed structures that are almost exactly circular.

It should also be understood that at least part of the end rings of the stent could be fabricated from or coated with a radiopaque metal such as tantalum or gold to provide a fluoroscopic indication of the stent position within a vessel. However, the other rings and the longitudinals could be made from a much less dense metal which would provide less obscuration of the central region within the stent. For example, the stent rings and longitudinals could all be fabricated from titanium or a titanium alloy except the end rings which could be formed from gold which is then plated with titanium. Thus, the entire outside surface of the stent would be titanium, which is known to be a comparatively non-thrombogenic metal while the gold in the end rings provides an improved fluoroscopic image of the stent extremities.

The dimensions of stent rings are typically 0.1 to 0.3 mm thick, with a width of 0.1 to 0.5 mm and an outside diameter D between 2.0 and 30.0; mm depending on the luminal diameter of the vessel into which it is inserted. The length of the stent could be between 1 and 10 cm. The wire diameter for the longitudinals would typically be between 0.05 and 0.5 mm.

Although the designs of FIGS. 1 through 7 inclusive illustrate separate longitudinals attached to a multiplicity of rings, this invention also contemplates an initial stent structure which is chemically etched from thin-walled tubing having an oval transverse cross section. Thus the oval and longitudinals would be formed from a single piece of metal thus precluding the need for attaching the longitudinals to the rings. In a similar manner laser or EDM machining could be used to form the stent from a thin-walled tube.

Figure 9:
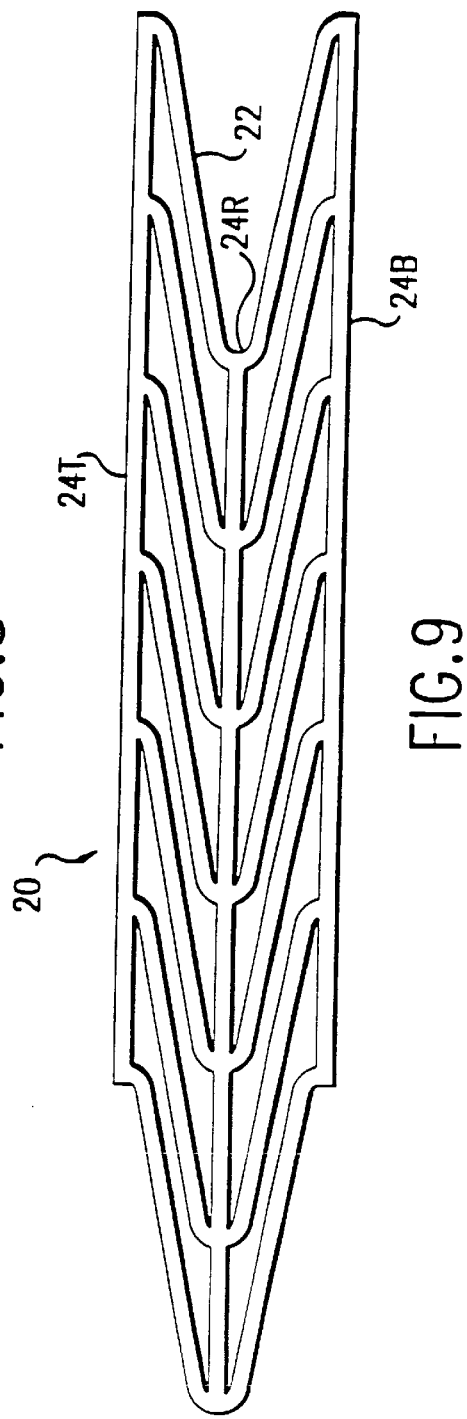
FIG. 9 is a side view of a stent as etched out of a small diameter metal cylinder as a single piece of metal.

It is further anticipated that a pre-deployment stent structure 20 as shown in FIG. 9 could be formed from a thin-walled cylindrical tube whose inside diameter is slightly smaller than the outside diameter of the balloon 6 shown in FIG. 6. A pattern such as that shown in either FIG. 6 or FIG. 7 could be photoetched onto a tin-walled metal cylinder. The one piece structure 20 shown in FIG. 9 has folded ovals 22 and longitudinals 23T, 24B, 24R and (not shown) 24L. This pre-deployment stent structure 20 could then be mounted onto the expandable balloon; the stent having sufficient elastic recoil to firmly grasp down onto the balloon. Another method to form the pre-deployment stent is by etching the correct pattern onto a thin, flat metal plate, then forming a tube from the plate and then making a longitudinal weld to form a cylindrically shaped structure which is, in fact, the pre-deployment stent structure 20 shown in FIG. 9.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A stent adapted for placement in the vessels of the human body, said stent comprising:

a thin-walled metal cylinder having a longitudinal axis, a proximal end and a distal end including a plurality of circumferentially relatively rigid portions, the relatively rigid portions being joined one to the other by one or more longitudinals extending in a substantially longitudinal direction, at least a portion of at least one of said longitudinals having an undulating shape wherein a first relatively rigid portion is located at the proximal end of the stent and a second relatively rigid portion is located at the distal end of the stent.

2. The stent as recited in claim 1 where at least one of said circumferentially relatively rigid portions defines a frame element having a substantially circumferential contour extending around said longitudinal axis.

3. The stent as recited in claim 2 where said at least one relatively rigid portion has a zig-zag contour extending throughout at least a portion of the circumferential extension of the relatively rigid portion.

4. The stent as recited in claim 1 where said at least one relatively rigid portion forms a circumferentially directed frame element.

5. The stent as recited in claim 2 where at least one of the said longitudinals is fixedly coupled to at least two longitudinally displaced frame elements.

6. The stent as recited in claim 2 where at least one of said longitudinals includes at least one undulating section and at least one substantially linearly directed section.

7. The stent as recited in claim 6 where at least one of said longitudinals includes a pair of substantially linearly directed sections formed integrally with and on opposing sides of said at least one undulating section.

8. A stent having a longitudinal axis, comprising:
   (a) a frame having a plurality of frame elements extending around said longitudinal axis of said stent, at least one of said frame elements having a circumferential contour extending at least partially external to a cross-sectional plane normal to said longitudinal axis; and,
   (b) a multiplicity of structures coupled to said frame, forming longitudinals and extending in a substantially longitudinal direction, at least a portion of at least one of said longitudinals having an undulating contour.

9. The stent as recited in claim 8 where at least one of said longitudinals is fixedly coupled to at least two longitudinally displaced frame elements.

10. The stent as recited in claim 8 where at least one of said longitudinals includes at least one undulating section and at least one substantially linearly directed section.

11. The stent as recited in claim 10 where at lest one of said longitudinals includes a pair of linearly directed sections formed integrally with and on opposing sides of said undulating section.

12. The stent as recited in claim 11 where each of said linearly directed sections is joined respectively to a pair of consecutively positioned and longitudinally displaced frame elements.

13. The stent as recited in claim 8 where at least one of said frame elements is formed in closed contour around said longitudinal axis of said stent.

14. The stent as recited in claim 8 where said frame and said longitudinals are formed from a thin-walled metal cylinder.

15. The stent as recited in claim 8 where at least one of said frame elements has at least one apex section, said at least one of said longitudinals being joined to said at least one of said frame elements at said apex section.

16. The stent as recited in claim 8 where at least two of said frame elements have a radiopacity value different than a radiopacity value of other frame elements forming said frame.

17. The stent as recited in claim 8 where said stent structure is formed from a metal having a shape memory characteristic.

18. The stent as recited in claim 8 where said frame is geometrically defined as a cylindrical envelope.

19. A stent having a longitudinal axis, comprising: at least two longitudinal structures each having at least one straight section and at least one undulating section, with each said straight section being joined to said at least one undulating section, the straight sections of all of the longitudinal structures being generally parallel to the longitudinal axis of the stent, the undulating section of each longitudinal structure extending generally in a circumferential direction and being of a generally curved shape so as to allow each undulating longitudinal structure to readily change length during insertion of the stent structure into a curved vessel of a human body.

20. A stent comprising:
   a plurality of longitudinal struts arranged circumferentially around said stent, said longitudinal struts having one or more undulating sections, each undulating section having a generally curved shape and having a first end point and a second end point wherein a line drawn from the first end point to the second end point is generally parallel to the stent's longitudinal axis, said longitudinals connected by a circumferentially extending structure configured to provide radial support to said stent.

21. A generally cylindrical stent having a circumference and a longitudinal axis, said stent having sufficient flexibility to permit said stent to be delivered percutaneously to curved coronary arteries, comprising:
   a plurality of circumferential elements, each of said circumferential elements extending around the circumference of the stent, and a plurality of connecting elements, each of said connecting elements having a first end and a second end, with the first end being fixedly connected to a first of said circumferential elements and the second end being fixedly connected to a circumferential element adjacent to said first circumferential element, where at least one of said connecting elements has an undulating section that can expand and contract in length while being passed through a curved coronary artery.

22. The stent of claim 21 where a line drawn from the first end of at least one connecting element to the second end of said at least one connecting element is substantially parallel to the stent's longitudinal axis.

23. The stent of claim 21 where at least one of said circumferential elements is formed integral with at least one of said connecting elements.

24. The stent of claim 21 where the stent is formed as an integral structure from a single piece of metal.

25. The stent of claim 21 where the stent is formed as an integral structure from a pre-existing metal tube.

26. The stent of claim 21 where each of said circumferential elements has at least two peaks and at least two valleys when the stent is in its pre-deployed shape.

27. The stent of claim 26 wherein the first end of at least one of said connecting elements is connected to a peak of one circumferential element and the second end of said connecting element is connected to a valley of an adjacent circumferential element.

28. The stent of claim 26 where each of said peaks and valleys are oriented along the longitudinal axis of the stent.

29. The stent of claim 21 where at least one of said connecting elements is straight and parallel to the longitudinal axis of the stent.

30. The stent of claim 21 including at least two connecting elements connecting adjacent circumferential elements.

31. A generally cylindrical stent having a circumference and a longitudinal axis, said stent having sufficient flexibility to permit said stent to be delivered percutaneously to curved coronary arteries, comprising: a plurality of circumferential elements, each of said circumferential elements extending around the circumference of the stent, and a plurality of connecting elements, each of said connecting elements having a first end and a second end, with the first end being fixedly connected to a first of said circumferential elements and the second end being fixedly connected to a circumferential element adjacent to said first circumferential element, whereby a line drawn from the first end of at least one connecting element to the second end of said at least one connecting element is substantially parallel to the stent's longitudinal axis and where at least one of said connecting elements has an undulating section that can expand and contract in length while being passed through a curved coronary artery.

32. The stent of claim 31 where at least one of said circumferential elements is formed integral with at least one of said connecting elements.

33. The stent of claim 31 where the stent is formed as an integral structure from a single piece of metal.

34. The stent of claim 31 where the stent is formed as an integral structure from a pre-existing metal tube.

35. The stent of claim 31 where each of said circumferential elements has at least two peaks and at least two valleys when the stent is in its pre-deployed shape.

36. The stent of claim 35 wherein the first end of at least one of said connecting elements is connected to a peak of one circumferential element and the second end of said connecting element is connected to a valley of an adjacent circumferential element.

37. The stent of claim 36 where each of said peaks and valleys are oriented along the longitudinal axis of the stent.

38. The stent of claim 31 where at least one of said connecting elements is straight and parallel to the longitudinal axis of the stent.

39. The stent of claim 31 including at least two connecting elements connecting adjacent circumferential elements.

40. A generally cylindrical stent having a circumference and a longitudinal axis, said stent having sufficient flexibility to permit said stent to be delivered percutaneously to curved coronary arteries, comprising:

a plurality of circumferential elements, each of said circumferential elements extending around the circumference of the stent, and a plurality of connecting elements, each of said connecting elements having a first end and a second end, with the first end being fixedly connected to a first of said circumferential elements and the second end being fixedly connected to a circumferential element adjacent to said first circumferential element, where at least one of said circumferential elements is formed integral with at least one of said connect elements and where at least one of said connecting elements has an undulating section that can expand and contract in length while being passed through a curved coronary artery.

41. The stent of claim 40 where a line drawn from the first end of at least one connecting element to the second end of said at least one connecting element is substantially parallel to the stent's longitudinal axis.

42. The stent of claim 40 where the stent is formed as an integral structure from a single piece of metal.

43. The stent of claim 40 where the stent is formed as an integral structure from a pre-existing metal tube.

44. The stent of claim 40 where each of said circumferential elements has at least two peaks and at least two valleys when the stent is in its pre-deployed shape.

45. The stent of claim 44 wherein the first end of at least one of said connecting elements is connected to a peak of one circumferential element and the second end of said connecting element is connected to a valley of an adjacent circumferential element.

46. The stent of claim 44 where each of said peaks and valleys are oriented along the longitudinal axis of the stent.

47. The stent of claim 40 where at least one of said connecting elements is straight and parallel to the longitudinal axis of the stent.

48. The stent of claim 40 including at least two connecting elements connecting adjacent circumferential elements.

49. A generally cylindrical stent having a circumference and a longitudinal axis, said stent having sufficient flexibility to permit said stent to be delivered percutaneously to curved coronary arteries, comprising:

a plurality of circumferential elements where each of said circumferential elements has at least two peaks and at least two valleys when the stent is in a pre-deployed state, each of said circumferential elements extending around the circumference of the stent, and a plurality of connecting elements, each of said connecting elements having a first end and a second end, with the first end being fixedly connected to a first of said circumferential elements and the second end being fixedly connected to a circumferential element adjacent to said first circumferential element, where at least one of said connecting elements has an undulating section that can expand and contract in length while being passed through a curved coronary artery.

50. The stent of claim 49 where a line drawn from the first end of at least one connecting element to the second end of said at least one connecting element is substantially parallel to the stent's longitudinal axis.

51. The stent of claim 49 where at least one of said circumferential elements is formed integral with at least one of said connecting elements.

52. The stent of claim 49 where the stent is formed as an integral structure from a single piece of metal.

53. The stent of claim 49 where the stent is formed as an integral structure from a pre-existing metal tube.

54. The stent of claim 49 wherein the first end of at least one of said connecting elements is connected to a peak of one circumferential element and the second end of said connecting element is connected to a valley of an adjacent circumferential element.

55. The stent of claim 49 where each of said peaks and valleys are oriented along the longitudinal axis of the stent.

56. The stent of claim 49 where at least one of said connecting elements is straight and parallel to the longitudinal axis of the stent.

57. The stent of claim 49 including at least two connecting elements connecting adjacent cumferential elements.

58. A generally cylindrical stent having a circumference and a longitudinal axis, said stent having sufficient flexibility to permit said stent to be delivered percutaneously to curved coronary arteries, comprising:

a plurality of circumferential elements, each of said circumferential elements extending around the circumference of the stent, and a plurality of connecting elements, each of said connecting elements having a first end and a second end, with the first end being fixedly connected to a first of said circumferential elements and the second end being fixedly connected to a circumferential element adjacent to said first circumferential element, where at least two of said connecting elements connect adjacent circumferential elements and where at least one of said connecting elements has an undulating section that can expand and contract in length while being passed through a curved coronary artery.

59. The stent of claim 58 where a line drawn from the first end of at least one connecting element to the second end of said at least one connecting element is substantially parallel to the stent's longitudinal axis.

60. The stent of claim 58 where at least one of said circumferential elements is formed integral with at least one of said connecting elements.

61. The stent of claim 58 where the stent is formed as an integral structure from a single piece of metal.

62. The stent of claim 58 where the stent is formed as an integral structure from a preexisting metal tube.

63. The stent of claim 58 where each of said circumferential elements has at least two peaks and at least two valleys when the stent is in its pre-deployed shape.

64. The stent of claim 63 wherein the first end of at least one of said connecting elements is connected to a peak of one circumferential element and the second end of said connecting element is connected to a valley of an adjacent circumferential element.

65. The stent of claim 63 where each of said peaks and valleys are oriented along the longitudinal axis of the stent.

66. The stent of claim 58 where at least one of said connecting elements is straight and parallel to the longitudinal axis of the stent.

* * * * *

UNITED STATES PATENT AND TRADEMARK OFFICE
CERTIFICATE OF CORRECTION

PATENT NO.   : 6,716,240 B2
DATED        : April 6, 2004
INVENTOR(S)  : Robert E. Fischell et al.

It is certified that error appears in the above-identified patent and that said Letters Patent is hereby corrected as shown below:

Title page,
Item [56], References Cited, OTHER PUBLICATIONS, please add the following:

Jury Verdict (Damages) of Cordis Corporation v. Boston Scientific Corporation and Scimed Life Systems, Inc. et al., Civil Action No. 97-550-SLR and Cordis Corporation v. Boston Scientific Corporations et al., Civil Action No. 98-197 (SLR)

Jury Verdict (Liability) of Cordis Corporation v. Boston Scientific Corporation and Scimed Life Systems, Inc. et al., Civil Action No. 97-550-SLR and Cordis Corporation v. Boston Scientific Corporations et al., Civil Action No. 98-197 (SLR)

November 20, 2000, Pretrial Hearing of Boston Scientific Corporation et al. v. Cordis Corporation, Civil Action No. 98-19 (SLR) and Cordis Corporation v. Boston Scientific Corporation et al., Civil Action No. 98-197 (SLR)

November 21, 2000, Trial Transcript of Boston Scientific Corporation et al. v. Cordis Corporation, Civil Action No. 98-19 (SLR) and Cordis Corporation v. Boston Scientific Corporation et al., Civil Action No. 98-197 (SLR)

November 27, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

November 28, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

November 29, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

November 30, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

December 1, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

December 4, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

December 5, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

December 6, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

December 7, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

December 8, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

UNITED STATES PATENT AND TRADEMARK OFFICE
CERTIFICATE OF CORRECTION

PATENT NO. : 6,716,240 B2
DATED : April 6, 2004
INVENTOR(S) : Robert E. Fischell et al.

It is certified that error appears in the above-identified patent and that said Letters Patent is hereby corrected as shown below:

Title page (cont'd),

December 11, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

December 12, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

December 13, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

December 14, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

December 15, 2000, Trial Transcript of Cordis Corporation v. Medtronic Ave., Inc. et al., Civil Action No. 97-550 (SLR) and Cordis Corporation v. Boston Scientific Corporation et al., Civil Action No. 98-197 (SLR)

February 9, 2001, Trial Transcript (Inequitable Conduct) of Cordis Corporation v. Medtronic Ave., Inc., et al., Civil Action No. 97-550 and Cordis Corporation v. Boston Scientific Corporation et al., Civil Action No. 98-197 (SLR)

February 12, 2001 Trial Transcript (Inequitable Conduct) of Cordis Corporation v. Medtronic Ave., Inc. et al., Civil Action No. 97-550 and Cordis Corporation v. Boston Scientific Corporation et al., Civil Action No. 98-197 (SLR)

March 28, 2002, Opinion re Post Trial Motions of Cordis Corporation v. Medtronic Ave., Inc., Civil Action No. 97-550 (SLR)

Cordis Corporation v. Boston Scientific Corporation and Scimed Life Systems, Inc., Brief in Support of BSC's Motions for Judgement as a Matter of Law with Respect to U.S. Patent Nos. 5,643,312 and 5,879,370, Civil Action No. 98-197-SLR Cordis Corporation v. Boston Scientific Corporation and Scimed Life Systems, Inc., Brief in Opposition to BSC's Motions for JMOL on the Fischell `312 and `370 Patents, Civil Action No. 98-197-SLR Cordis Corporation v. Boston Scientific Corporation and Scimed Life Systems, Inc., BSC's Reply Brief in Support of BSC's Motions for Judgement as a Matter of Law with Respect to U.S. Patent Nos. 5,643,312 and 5,879,370, Civil Action No. 98-197-SLR Cordis Corporation v. Boston Scientific Corporation and Scimed Life Systems, Inc., Opening Brief in Support of Cordis' JMOL Motion Against Boston Scientific on Claim 44 of the Palmaz `762 Patent and Claim 25 of the Fischell `370 Patent, Civil Action No. 98-197-SLR Cordis Corporation v. Boston Scientific Corporation and Scimed Life Systems, Inc., BSC's Brief in Opposition To Cordis' JMOL Motion Regarding the Applicability of the Reverse Doctrine of Equivalents to Claim 25 of U.S. Patent No. 5,879,370, Civil Action No. 98-197-SLR

UNITED STATES PATENT AND TRADEMARK OFFICE
CERTIFICATE OF CORRECTION

PATENT NO. : 6,716,240 B2
DATED : April 6, 2004
INVENTOR(S) : Robert E. Fischell et al.

It is certified that error appears in the above-identified patent and that said Letters Patent is hereby corrected as shown below:

Title page (cont'd),

Cordis Corporation v. Boston Scientific Corporation and Scimed Life Systems, Inc., Reply Brief in Support of Cordis' Motion for JMOL Against BSC on Claim 44 of The Palmaz '762 Patent and Claim 25 of the Fischell '370 Patent, Civil Action No. 98-197-SLR Cordis Corporation v. Boston Scientific Corporation and Scimed Life Systems, Inc., BSC's Post-Trial Brief in Support of Finding that U.S. Patent Nos. 5,643,312 and 5,879,370 are Unenforceable due to Inequitable Conduct, Civil Action No. 98-197 (SLR), Civil Action No. 98-197-SLR Cordis Corporation v. Boston Scientific Corporation and Scimed Life Systems, Inc., BSC's Reply Brief in Support of Finding That U.S. Patent Nos. 5,643,312 and 5,879,370 are Unenforceable due to Inequitable Conduct, Civil Action No. 98-197-SLR Cordis Corporation v. Boston Scientific Corporation and Scimed Life Systems, Inc., Reply Brief in Support of Defendants' Motion for Summary Judgment of Unenforceability due to Inequitable Conduct, Civil Action No. 98-197-SLR Cordis Corporation v. Boston Scientific Corporation and Scimed Life Systems, Inc., Defendants' Markman Memorandum on Claim Construction, Civil Action No. 98-197-SLR Cordis Corporation v. Boston Scientific Corporation and Scimed Life Systems, Inc., Reply Brief in Support of Defendants' Motion for Summary Judgement of Invalidity Under 35 U.S.C. Section 112, Paragraph 2 (Claim Indefiniteness), Civil Action No. 98-197-SLR Cordis Corporation v. Boston Scientific Corporation and Scimed Life Systems, Inc., Reply Brief in Support of Defendant's Motion for Summary Judgement of Noninfringement, Civil Action No. 98-197-SLR Cordis Corporation v. Boston Scientific Corporation and Scimed Life Systems, Inc., Opening Export Report of David C. Cumberland, M.D., Civil Action No. 98-197-SLR Cordis Corporation v. Boston Scientific Corporation and Scimed Life Systems, Inc., Rebuttal Export of David C. Cumberland, M.D., Civil Action No. 98-197-SLR Cordis Corporation v. Boston Scientific Corporation and Scimed Life Systems, Inc., Supplemental Export Report of David C. Cumberland, M.D., Civil Action No. 98-197-SLR Cordis Corporation v. Boston Scientific Corporation and Scimed Life Systems, Inc., Opening Expert Report of Andrew S. Douglas, Ph.D., Civil Action No. 98-197-SLR Cordis Corporation v. Boston Scientific Corporation and Scimed Life Systems, Inc., Rebuttal Expert Report of Andrew S. Douglas, Ph.D., Civil Action No. 98-197-SLR Cordis Corporation v. Boston Scientific Corporation and Scimed Life Systems, Inc., Supplemental Expert Report of Andrew S. Douglas, Ph.D., Civil Action No. 98-197-SLR Cordis Corporation v. Boston Scientific Corporation and Scimed Life Systems, Inc., Boston Scientific Corporation and Scimed Life Systems, Inc.'s Notice Pursuant to 35 U.S.C. § 282, Civil Action No. 97-550-SLR and Cordis Corporation v. Boston Scientific Corporation et al., Civil Action No. 98-197 (SLR)

Cordis Corporation v. Boston Scientific Corporation and Scimed Life Systems, Inc., Memorandum Order dated September 7, 2000, Civil Action No. 98-197-SLR Cordis Corporation v. Boston Scientific Corporation and Scimed Life Systems, Inc., Order dated November 1, 2000 Denying Defendant's Motion for Summary Judgment of Invalidity, Civil Action No. 98-197-SLR

UNITED STATES PATENT AND TRADEMARK OFFICE
CERTIFICATE OF CORRECTION

PATENT NO. : 6,716,240 B2
DATED : April 6, 2004
INVENTOR(S) : Robert E. Fischell et al.

It is certified that error appears in the above-identified patent and that said Letters Patent is hereby corrected as shown below:

Title page (cont'd),

Cordis Corporation v. Boston Scientific Corporation and Scimed Life Systems, Incl, Order dated November 1, 2000 Summary Judgment of Infringement, Civil Action No. 98-197-SLR Cordis Corporation v. Boston Scientific Corporation and Scimed Life Systems, Inc., Deposition of Robert E. Fischell, Ph.D dated November 16, 1999, Civil Action No. 98-197-SLR Cordis Corporation v. Boston Scientific Corporation and Scimed Life Systems, Inc., Deposition of Robert E. Fischell, Ph.D dated January 4, 2000, Civil Action No. 98-197-SLR Cordis Corporation v. Boston Scientific Corporation and Scimed Life Systems, Inc., Deposition of Robert E Fischell, Ph.D dated January 5, 2000, Civil Action No. 98-197-SLR Cordis Corporation v. Boston Scientific Corporation and Scimed Life Systems, Inc., Deposition of Robert E. Fischell, Ph.D dated January 6, 2000, Civil Action No. 98-197-SLR Cordis Corporation v. Boston Scientific Corporation and Scimed Life Systems, Inc., Deposition of Robert E. Fischell, Ph.D dated January 6, 2000, Civil Action No. 98-197-SLR Cordis Corporation v. Boston Scientific Corporation and Scimed Life Systems, Inc., Deposition of Robert E. Fischell, Ph.D dated June 15, 2000, Civil Action No. 98-197-SLR Cordis Corporation v. Boston Scientific Corporation and Scimed Life Systems, Inc., Deposition of Morton Rosenberg, Esq. dated February 3, 2000, Civil Action No. 98-197-SLR Cordis Corporation v. Boston Scientific Corporation and Scimed Life Systems, Inc., Deposition of Morton Rosenberg, Esq. dated June 15, 2000, Civil Action No. 98-197-SLR Signed and Sealed this Tenth Day of August, 2004

JON W. DUDAS
*Acting Director of the United States Patent and Trademark Office*